United States Patent
Lipman et al.

(10) Patent No.: US 6,669,675 B2
(45) Date of Patent: *Dec. 30, 2003

(54) FEMININE URINARY DEVICE

(76) Inventors: Vivian Lipman, 1000 Uptown Park Blvd.-#231, Houston, TX (US) 77056; Joyce Nimetz, 5638 Jason, Houston, TX (US) 77096

( * ) Notice: Subject to any disclaimer, the term of this patent is extended or adjusted under 35 U.S.C. 154(b) by 0 days.

This patent is subject to a terminal disclaimer.

(21) Appl. No.: 10/287,840

(22) Filed: Nov. 4, 2002

(65) Prior Publication Data

US 2003/0088218 A1 May 8, 2003

Related U.S. Application Data

(63) Continuation-in-part of application No. 09/694,596, filed on Oct. 23, 2000, now Pat. No. 6,475,198.

(51) Int. Cl.[7] .................... A47K 11/02; A61F 5/44; A61F 13/15; A61B 5/00
(52) U.S. Cl. .............. 604/329; 4/144.4; 4/144.1; 4/144.3; 600/574; 604/358
(58) Field of Search ............... 604/329, 385.01, 604/385.02, 327; 4/144.1–144.4; 600/574

(56) References Cited

U.S. PATENT DOCUMENTS

| 2,878,486 | A | * | 3/1959 | Bartlett et al. ............... 4/110 |
| 4,756,029 | A | * | 7/1988 | Zieve et al. ................. 4/144.4 |
| 5,401,263 | A | * | 3/1995 | Cornellier ................... 604/329 |
| 5,966,748 | A | * | 10/1999 | Young et al. ............... 4/144.4 |
| 6,475,198 | B1 | * | 11/2002 | Lipman et al. ............. 604/329 |

* cited by examiner

Primary Examiner—Weilun Lo
Assistant Examiner—Jacqueline F Stephens
(74) Attorney, Agent, or Firm—Larry J. Guffey

(57) ABSTRACT

A feminine urinary device is disclosed. It comprises a thin, water resistant sheet having a front and a portion. The size and shape of these are such as to allow a user to place the rear portion between her legs while grasping the edges of the front portion so as to turn these edges upward so as to form a trough for directing the direction of discharge of her urine. A tissue and water impermeable envelope for storing the device are also provided. The device allows a female to comfortably urinate while standing, thereby eliminating the problems associated unsanitary or unavailable restroom facilities.

4 Claims, 9 Drawing Sheets

FEMININE URINARY DEVICE

CROSS-REFERENCE TO RELATED APPLICATION

This application is a continuation-in-part and is related to U.S. patent application Ser. No. 09/694,596, filed Oct. 23, 2000, which will issue on Nov. 5, 2002 as U.S. Pat. No. 6,475,198.

BACKGROUND OF THE INVENTION

1. Field of the Invention

The present invention generally relates to a means for collecting bodily waste materials. More particularly, this invention relates to a feminine urinary device that allows a human female to comfortably urinate while standing.

2. Description of the Related Art

There are many instances in which sanitary facilities for female urination are unavailable in the sense of being either unsanitary, overcrowded or completely lacking. For example, at public events such as concerts or sporting events, the facilities provided often have less than desired cleanliness or availability. When camping or hiking, for example, facilities are often completely lacking.

Although this problem appears to be widely recognized, there have been few patents issued which seek to provide a means for resolving the problem. The exception appearing to be U.S. Pat. No. 5,401,263. It discloses a feminine urinary aid package that includes a closed flat enclosure that is constructed to be opened by a user. This package includes a one piece body having a pair of side portions and a triangular end portion that is integrally joined to the side portions. When opened, it imparts an open V-shaped cross section that aids a user in directing one's path of urination.

Despite the apparent limited prior art, there exists a continuing need for an improved means for allowing a human female to comfortably urinate while standing.

SUMMARY OF THE INVENTION

One embodiment of a feminine urinary device in accordance with the present invention includes a thin, water resistant sheet having a front and a portion. The size and shape of these are such as to allow a user to place the rear portion between her legs while grasping the edges of the front portion so as to turn these edges upward so as to form a trough for directing the direction of discharge of her urine. A tissue and water impermeable envelope for storing the device are also provided.

Thus, there has been summarized above, rather broadly, the more important features of the present invention in order that the detailed description that follows may be better understood and appreciated. There are, of course, additional features of the invention that will be described hereinafter and which will form the subject matter of the claims appended thereto.

In this respect, before explaining at least one embodiment of the present invention in detail, it is to be understood that the invention is not limited in its application to the details of the embodiments set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other devices and methods for carrying out the several purposes of the present invention. It is important, therefore, that the claims be regarded as including such equivalent constructions insofar as they do not depart from the spirit and scope of the present invention.

It is therefore an object of the present invention to provide a new and improved, feminine urinary device that allows a female to comfortably urinate while standing.

It is another object of the present invention to provide a feminine device that will aid a female in performing excremental body functions while standing.

It is yet another object of the present invention to provide a feminine device that will aid a female in performing excremental body functions without soiling her clothes when restroom facilities are unsanitary or unavailable.

It is a further object of the present invention to provide a feminine urinary aid package that may be readily sold in quantity in a box or individually, or in a dispensing machine, and is particularly well suited for transport in a purse, back-pack or the like.

It is a still further object of the present invention to provide a reusable, feminine urinary device.

These and other objects and advantages of the present invention will become readily apparent as the invention is better understood by reference to the accompanying drawings and the detailed description that follows.

DESCRIPTION OF THE PREFERRED EMBODIMENT

Figure 1:
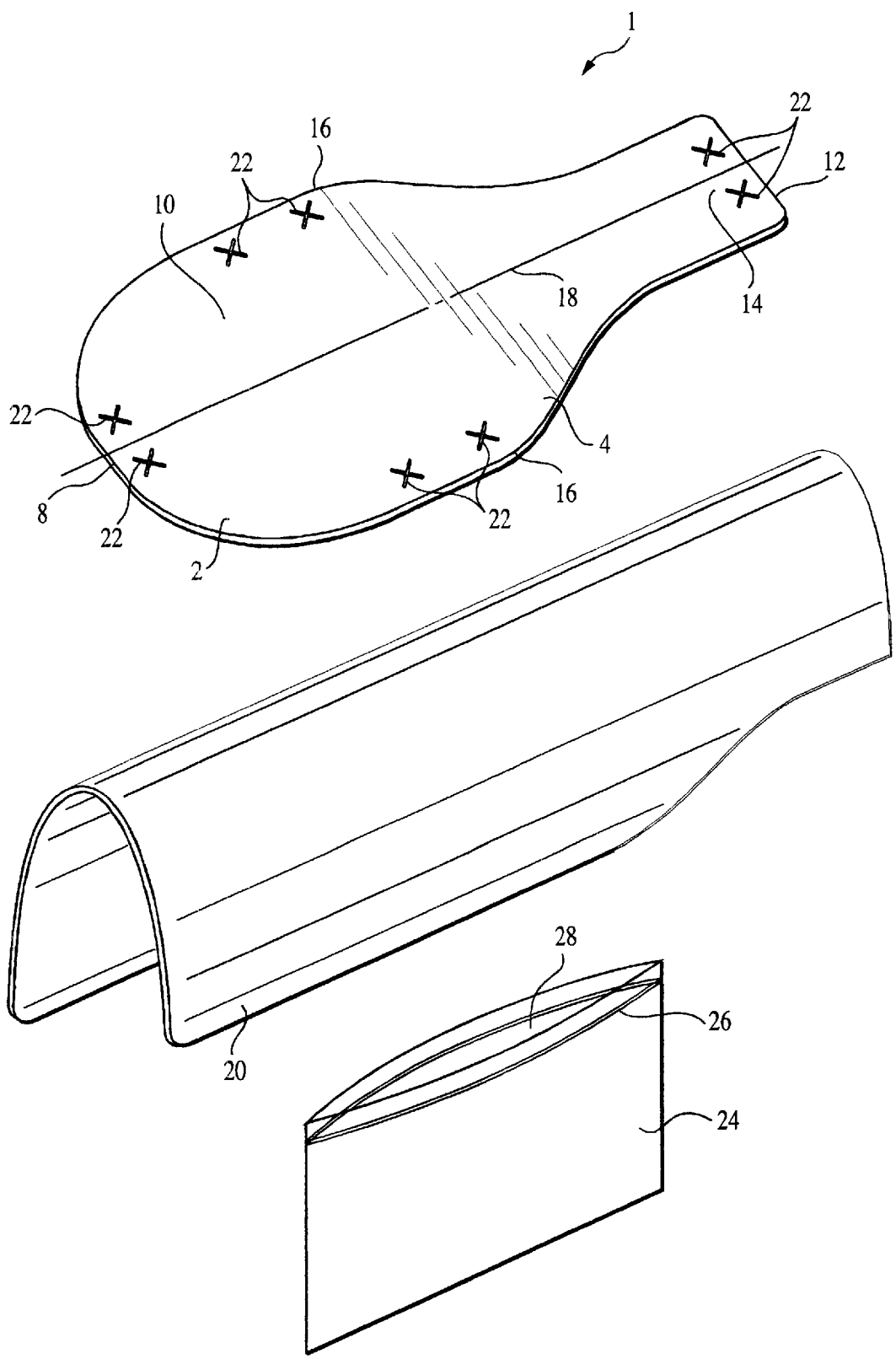
FIG. 1 is a perspective view of a preferred embodiment of the present invention.

Referring now to the drawings wherein are shown preferred embodiments and wherein like reference numerals designate like elements throughout, there is shown in FIG. 1 a top view of an embodiment of the present invention in the form of a feminine urinary device.

In this embodiment, the feminine urinary device 1 consists of an elongated, thin, water resistant sheet 2 having a top 4 and a bottom 6 surface, a front end 8 adjoining a front portion 10, a rear end 12 adjoining a rear portion 14, and side edges 16 with a centerline 18 extending between the ends.

Figure 2:
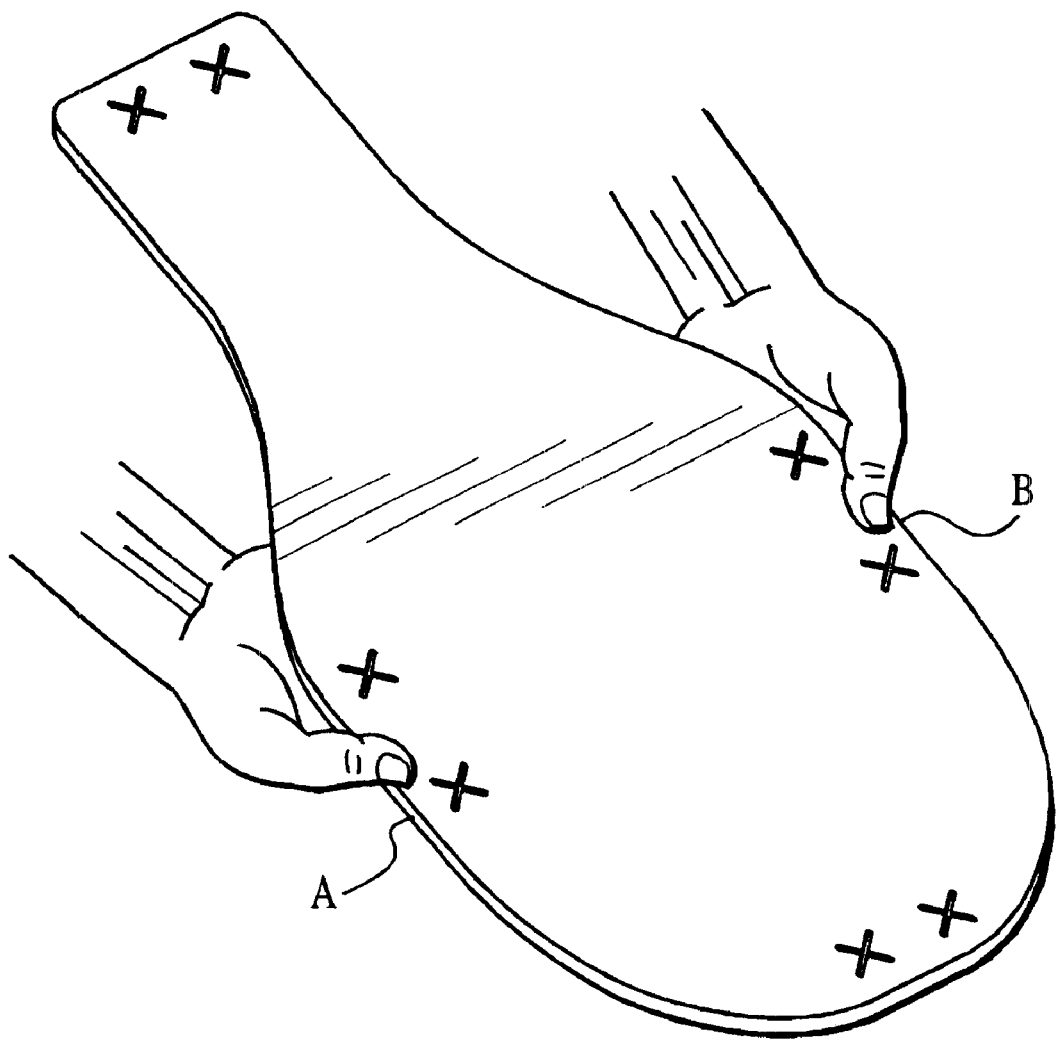
FIG. 2 is a top view of the present invention illustrating how a user holds the sheet during use.

The size and shape of the rear portion 14 of the sheet 2 are configured so as to allow a user to comfortably place and hold, in essentially a horizontal plane, the rear portion 14 of the sheet 2 between the user's legs when it is being used. Meanwhile, the side edges 16 of the front portion 10 of the sheet 2 are flared outward from the centerline 18 so as to allow a user to hold with her hands the edges 16 of the front portion 10 of the sheet 2 at a safe distance from the sheet's centerline 18 so that a user's hands are not at risk of being soiled when the device 1 is being used. This additional width of the front portion 10 of the sheet 2 also allows a user, when using the device, to turn upward the portion of the sheet proximate the front portion edges 16 so as to form a trough for directing the direction of discharge of a user's excrements. See FIG. 2.

Figure 3:
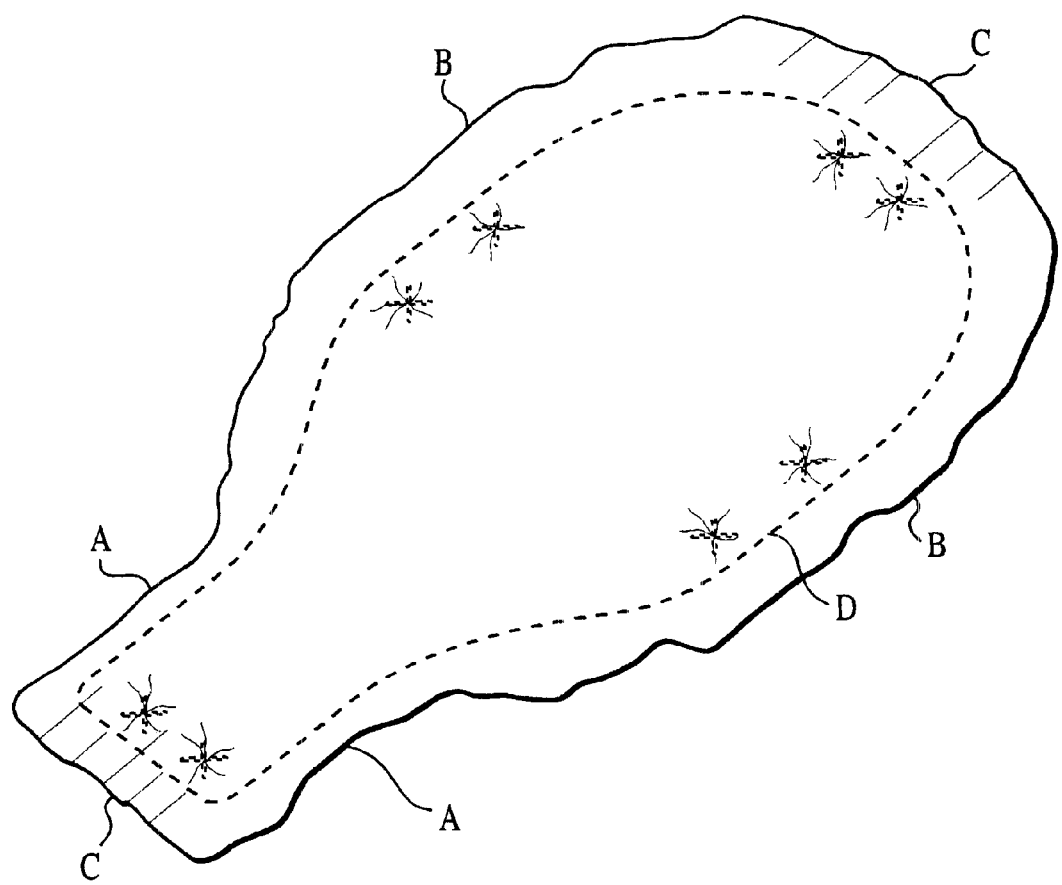
FIG. 3 is a top view of the present invention illustrating the use of a disposable tissue placed on the device's top surface.
Figure 4A:
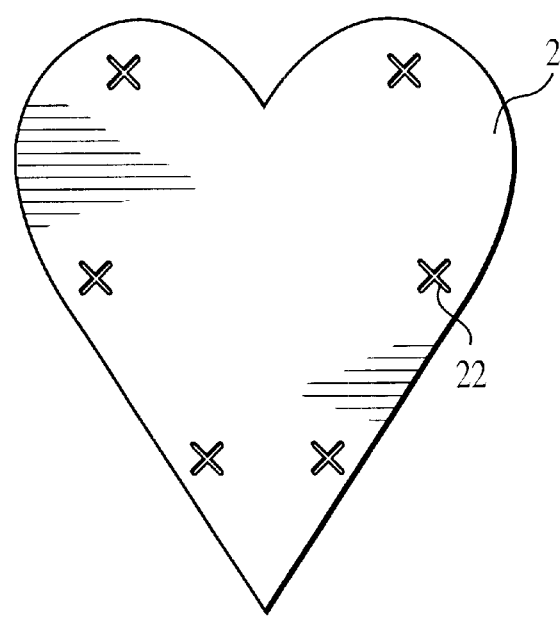
FIGS. 4(a)–4(j) are top views of an assortment of alternative, sheet shapes which have a flared front portion and are part of preferred embodiments of the present invention.
Figure 4B:
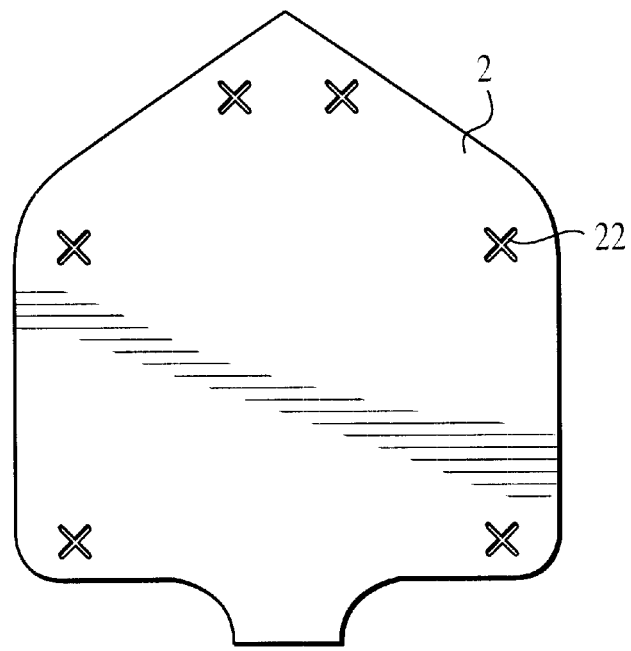
Figure 4C:
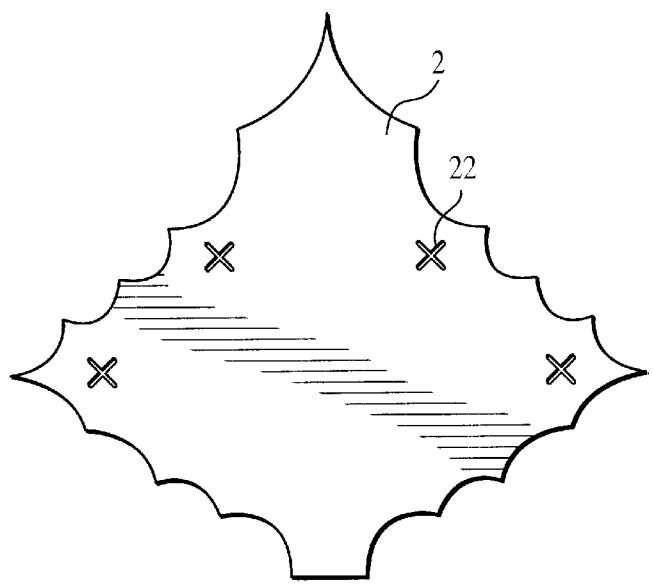
Figure 4D:
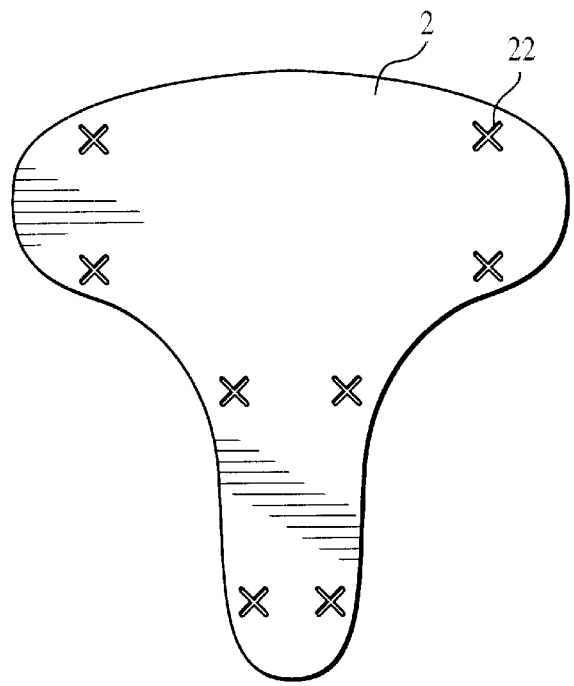
Figure 4E:
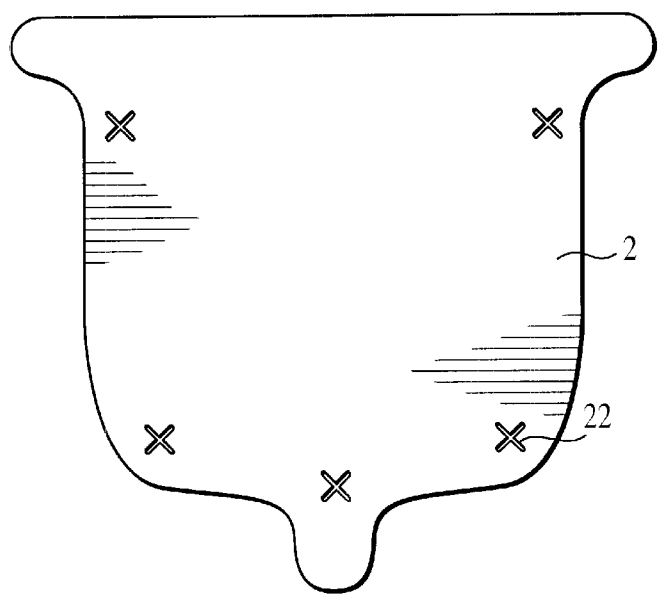
Figure 4F:
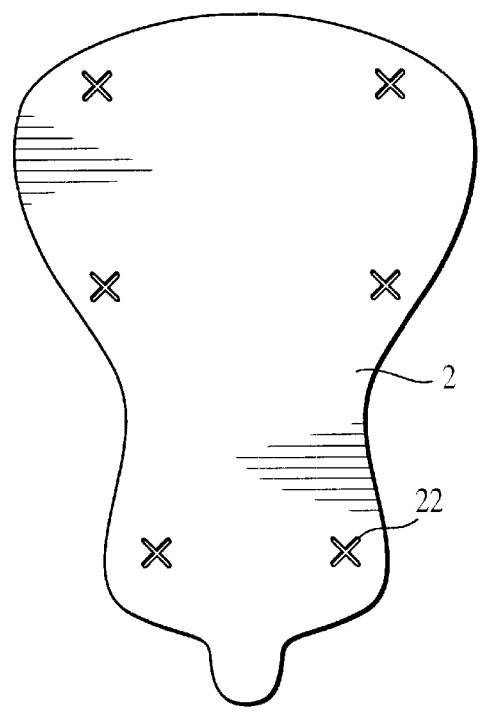
Figure 4G:
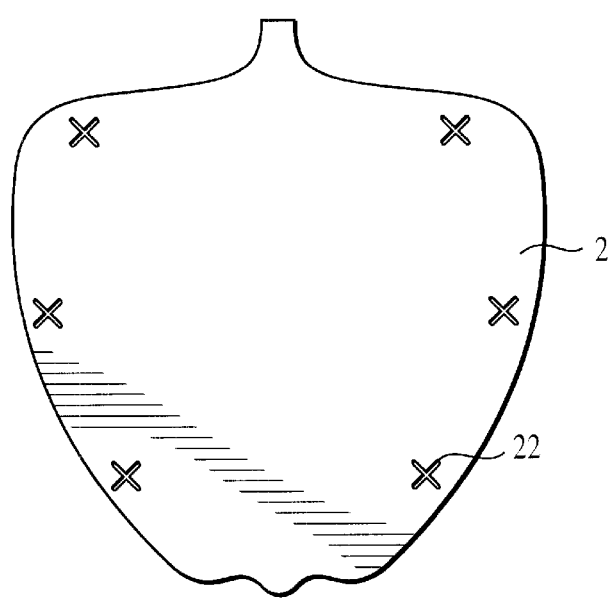
Figure 4H:
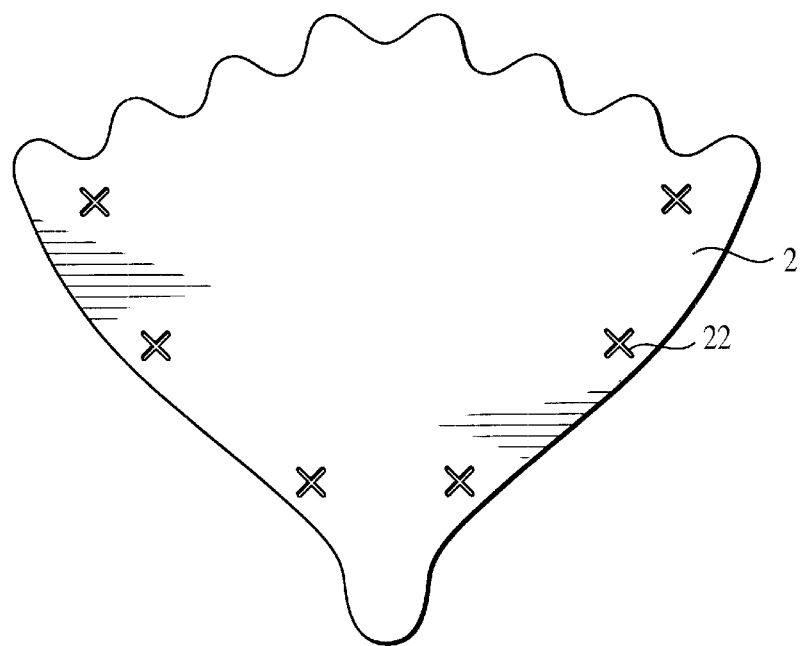
Figure 4I:
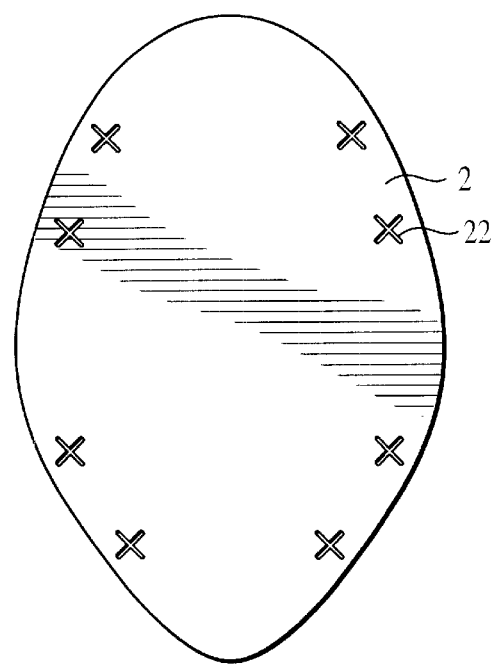
Figure 4J:
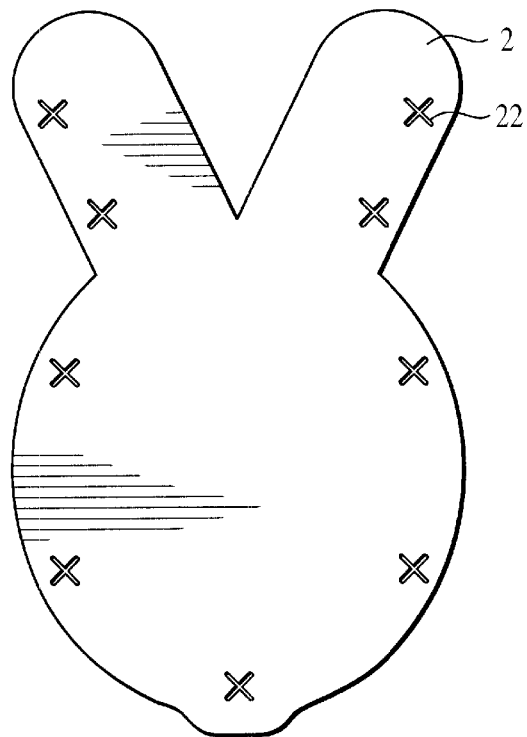

For cleanliness purposes and to aid in cleaning the device 1 after its use, a biodegradable tissue 20 is provided for placement on the top surface of the sheet 2 when it is in use. To secure this tissue 20 in place on the sheet 2, the sheet 2 is provided with a number of slots 22 into which portions of the tissue 20 are fitted. FIG. 3 shows this tissue 20 in use.

In order to comfortably store the sheet 2 when it is being transported, a water impermeable, flat envelope 24 is provided. The configuration and shape of this envelope is such as to easily accommodate the sheet when it has been tightly rolled along its centerline. For an adult-size sheet 2, a rectangular envelope of approximately 4.0×7.0 inches or 7.0×8.0 inches is seen to be suitable. A zip-lock tap 26 surrounding the envelope's opening 28 provides a convenient means for sealing the envelope 24.

For the embodiment shown in FIG. 1, the sheet 2, in a size suitable for use by an adult female, is seen to have a rear portion 14 that is approximately 2.5 to 3.5 inches wide and 2.5 to 3.5 inches in length. The front portion 10 of the sheet is seen to take an approximately elliptical shape, with a major axis, along the sheet's centerline, that is approximately 7.5 to 9.0 inches and a minor axis, across the width of the sheet, that is approximately 6.0 to 9.0 inches in length. From the sheet's front 8 to its rear 12 end, it has an overall length of approximately 10.5 to 12.5 inches.

For a sheet of this size, its accompanying a biodegradable tissue 20 would typically have a size of approximately 13 inches wide by 17 inches in length.

A total of eight slots are provided in the sheet 2, with a pair of such slots being located proximate the front and rear ends, and proximate either edge of the front portion of the sheet. The individual slots are configured in an X-shape so as to make it easy to stuff and hold a portion of the tissue 20 in the slots.

A large number of materials are suitable from which to construct the sheet 2 of the present invention. For example, a sheet of approximately 1/32 to 1/4 inch thickness and made from a type of foamed plastic material and having a smooth, soft, water and odor impermeable outer surfaces, has been shown to be quite satisfactory for the purposes of the present invention. This material is quite flexible, and can be easily and tightly rolled so as to form a minimum volume sheet for storage when not in use, but it will quickly regain its essentially flat shape after storage for extended periods of time. Such a material is available from many manufacturers, including F. W. Kraemer, Remscheid, Germany.

For reuse, the sheet 2 is easily cleaned by a citrus-scented, water-based mixture of a washing soap (e.g., Arm & Hammer) and vinegar (e.g., to one gallon of water, add one cup of both soap and vinegar and one ounce of a citrus oil).

It should be noted that, in addition to urinary purposes, the present invention is seen to also be of assistance to one who wishes to perform a bowel movement while standing with attention being given to exactly where the user's discharge is directed.

To use the present invention, a user removes the sheet and tissue from its storage envelope. Portions of the tissue are pushed into the sheet's slots so as to hold the tissue in place on the sheet's top surface. Grasping and turning upward the sheet's outer edges, a trough is formed for directing a user's discharge. After use, the tissue is disposed of and the sheet wiped dry, rolled-up and returned to its storage envelope At a convenient, later time, the sheet is washed and stored, along with a new tissue, in its storage envelope for later use.

In addition to the preferred embodiment shown in FIG. 1, it has been found that many similar shapes will suffice for the sheet 2 and tissue 20. For example, FIGS. 4(*a*)–(*j*) reveal an assortment of sheet shapes which have a flared front portion and which may have particular value in marketing the present invention. These may generally be described as shaped like a: (a) heart, (b) Hanukah dradle, (c) holly wreath, (d) paddle, (e) bell, (f) pear, (g) apple, (h) fan, (i) oval or egg, and (J) bunny rabbit head.

Figure 5:
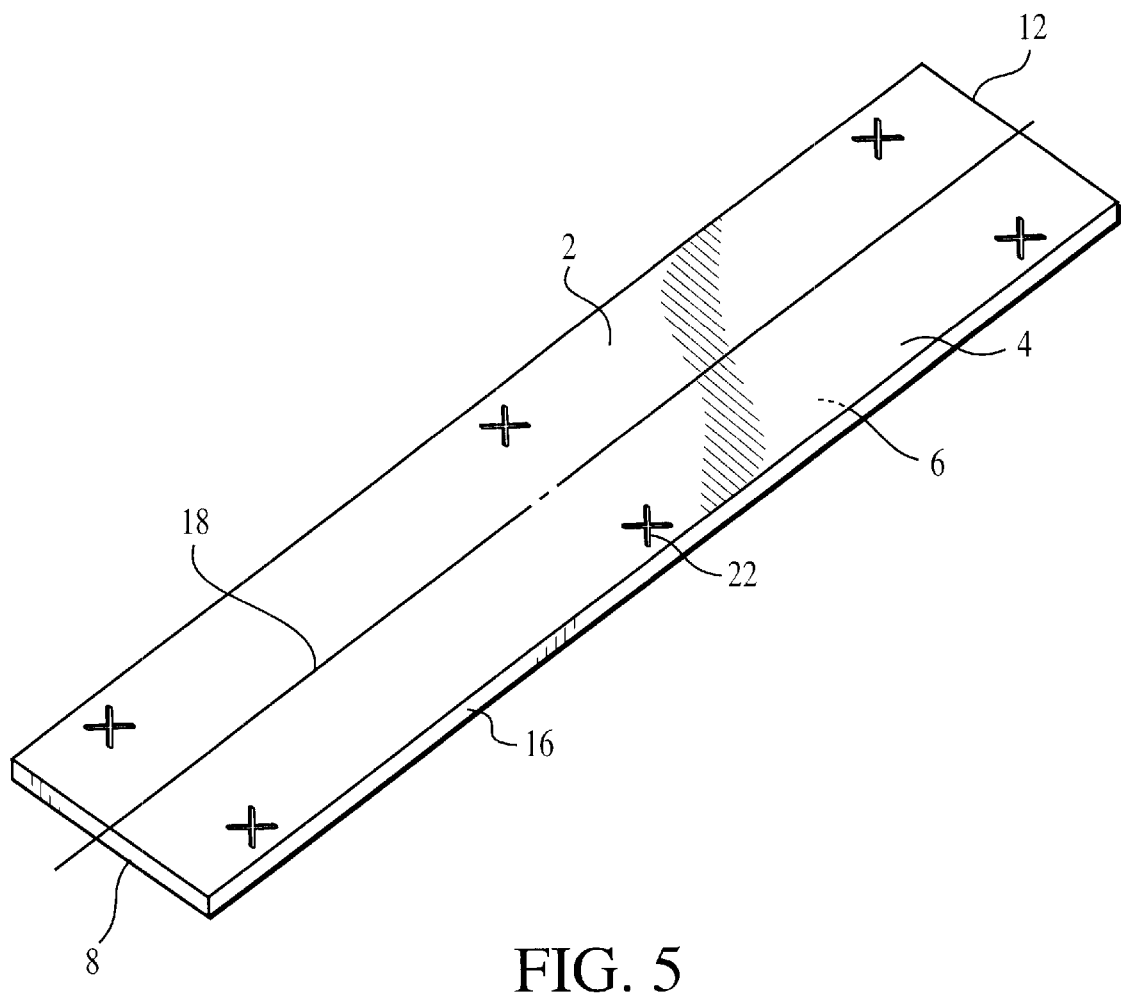
FIG. 5 is a top view of another alternative, sheet shape which does not have a flared front portion and which is part of preferred embodiments of the present invention.

Additionally, continued evaluation of various, early prototypes of the present invention have been found that even shapes for this invention's water resistant sheet 2 which have little or no flaring of the front portion of the sheet 2 can still be handled by most users so as to make these shapes workable in the context of the present invention. FIG. 5 shows a preferred embodiment for the water resistant sheet 2 of the present invention which has very little variation of the sheet's width from its front 8 to rear 12 end.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention as hereinafter set forth in the claims.

We claim:

1. A feminine urinary device comprising:
   a thin, water resistant sheet having a top and a bottom surface, a front end adjoining a front portion, a rear end adjoining a rear portion, and side edges with a centerline extending between said ends,
   wherein the size and shape of said rear portion of said sheet being such as to allow a user to place said rear portion between said user's legs when said device is used and said top surface is held in a generally horizontal plane,
   wherein said side edges of said front portion are configured so as to allow a user to hold with her hands said front portion, side edges and have the user's hands be a distance from said centerline that is at least as great as the distance from said centerline to said side edges for said rear portion of said sheet, and the size and the shape of said front portion of said sheet being such as to allow a user when using said device to turn upward said front portion side edges so as to form a trough for directing the direction of discharge of said user's excrements, a biodegradable tissue for placement on said sheet top surface when said sheet is in use, wherein said sheet further having a plurality of slots therein and into which portions of said tissue are placed so as to secure the placement of said tissue to said sheet top surface.

2. A feminine urinary device as recited in claim 1, further comprising:

a water impermeable, flat envelope constructed to be opened by said user for storing said sheet when not in use.

3. A feminine urinary device as recited in claim 1, wherein said sheet having a thickness in the range of $\frac{1}{32}$ to $\frac{1}{4}$ inches and is made from a foamed plastic material.

4. A feminine urinary device as recited in claim 2, wherein said sheet having a thickness in the range of $\frac{1}{32}$ to $\frac{1}{4}$ inches and is made from a foamed plastic material.

* * * * *